United States Patent [19]

Leclerc et al.

[11] 4,344,935

[45] Aug. 17, 1982

[54] PROCESS FOR THE ISOLATION OF VIRAL GLYCOPROTEIC ANTIGENS AND ITS APPLICATION TO THE PREPARATION OF VACCINES

[75] Inventors: Jean Leclerc, Libourne; Jean de Rudder, Versailles, both of France

[73] Assignee: Synthelabo, Paris, France

[21] Appl. No.: 265,084

[22] Filed: May 19, 1981

[30] Foreign Application Priority Data

Jun. 5, 1980 [FR] France ................ 80 12522

[51] Int. Cl.$^3$ .................. A61K 39/12; A61K 39/145
[52] U.S. Cl. ................ 424/89; 424/235; 424/236; 424/238; 424/239
[58] Field of Search .................. 424/89, 235–239

[56] References Cited

U.S. PATENT DOCUMENTS

| | | | |
|---|---|---|---|
| 3,629,470 | 12/1971 | Kanarek et al. | 424/89 |
| 3,630,840 | 12/1971 | Wagner et al. | 435/239 |
| 3,790,552 | 2/1974 | Johnson et al. | 424/89 |
| 3,847,737 | 11/1974 | Kanarek | 424/89 |
| 3,951,937 | 4/1976 | Unek et al. | 435/239 |
| 3,962,421 | 6/1976 | Neurath | 424/89 |
| 3,989,818 | 11/1976 | Polson | 424/89 |
| 4,064,232 | 12/1977 | Bachmayer et al. | 424/89 |
| 4,140,762 | 2/1979 | Bachmayer et al. | 424/89 |
| 4,206,014 | 6/1980 | Reichert et al. | 424/89 |

FOREIGN PATENT DOCUMENTS

| | | |
|---|---|---|
| 1365 | 4/1979 | European Pat. Off. . |
| 11168 | 5/1980 | European Pat. Off. . |
| 1587316 | 3/1974 | France . |
| 2248054 | 5/1975 | France . |
| 2297635 | 8/1976 | France . |
| 2422720 | 9/1979 | France . |

OTHER PUBLICATIONS

Snipes et al, Chem. Abstr. 92: 221x (1980) of Symp. Pharmacol. of Eff. Lipids (pap) 1978: 63–73.
Sands et al, Chem. Abstr. 90: 133352w and 180765t (1979) of Antimicrob. Agents Chemother. (1979) 15(1): 67–73 and 134–136.
Snipes et al, Chem. Abstr. 86: 101389g (1977) of Antimicrob. Agents Chemother. (1977) 11(1): 98–104.
Larin et al, Chem. Abstr. 74: 138637x (1971) of J. HY6, 1971, 69 (1): 35–46.
Ventura et al., Chem. Abstr. 73: 32698g (1970) of P.S.E.B.M., 1970, 133 (2): 711–717.
Corbel et al, Chem. Abstr. 73: 23530m and 11653y, (1970) of J. HY6, 1970, 68 (1): 81–96 and 77–80.
"Chemical Abstracts", vol. 84, No. 17, Apr. 26, 1976, 118233r, p. 250.
"Nature", vol. 276, No. 5689, Dec. 1978, pp. 715–718.

*Primary Examiner*—Shep K. Rose
*Attorney, Agent, or Firm*—Young & Thompson

[57] ABSTRACT

Process for the isolation of the glycoproteic antigens of a virus by treatment of said virus with an aqueous solution of a nonionic detergent, separation of the viral particles and removal of the detergent, comprising, in order to remove the detergent, effecting a phase separation between an aqueous phase and a phase consisting of a water-insoluble higher alcohol, and recovering the glycoproteic antigens in aqueous phase.

11 Claims, No Drawings

PROCESS FOR THE ISOLATION OF VIRAL GLYCOPROTEIC ANTIGENS AND ITS APPLICATION TO THE PREPARATION OF VACCINES

This invention relates to the preparation of antigens extracted from viruses, particularly from influenza viruses, for the purpose of producing vaccines to immunize humans or animals against said viruses.

Certain types of viruses (Myxovirus, Paramyxovirus, Rhabdovirus, leukosis virus, etc.) are coated with a lipidic membrane in which are bound glycoproteins which, for example in the case of influenza virus, constitute the antigens which make vaccination against such viruses possible.

Said glycoproteic antigens are selectively solubilized with various aqueous detergent solutions, particularly nonionic detergents such as Triton X-100. It is then possible, by means of various methods such as centrifugation, exclusion, and the like, to separate such antigens—which have been solubilized in the detergent solution— from the remainder of the viral particle whose proteins are not useful for the preparation of vaccines.

The glycoproteins must then be separated from the detergent, while maintaining their immunological and functional characteristics which make their characterization possible: e.g., the enzymatic neuraminidase activity and the hemagglutinating activity of hemagglutinine. Such glycoproteins should be titrable by radial immunodiffusion and should be found immunogenic.

Various methods have already been suggested for the separation of glycoproteins from detergents. Thus, Scheid and co-workers (Virology 50, 640–652, 1972) precipitate glycoproteins from their aqueous solution by addition of butanol. This leads to a partial denaturation of the glycoproteins.

Holloway (Analytical Biochemistry 53, 304–308, 1973) suggests using styrene-divinylbenzene copolymer beads to adsorb the nonionic detergent, the glycoproteins remaining dissolved in the aqueous phase. This technique is relatively complex to carry out.

Applicant has found that viral glycoproteic antigens may be separated from the nonionic detergents used to remove them from the virus, by means of a phase separation between an aqueous phase and a phase consisting of a water-insoluble higher alcohol.

It was surprisingly found that such a treatment does not deleteriously affect the properties of the glycoproteins which may thus be used for the preparation of a specific vaccine, against influenza, for example.

Therefore, this invention relates to a process for the isolation of glycoprotein antigens from a virus by treatment of the virus with an aqueous solution of a nonionic detergent, separation of the viral particles and removal of the detergent, comprising, in order to remove the detergent, effecting a phase separation between an aqueous phase and a phase consisting of a water-insoluble higher alcohol, and recovering the glycoproteic antigens in aqueous phase.

The nonionic detergent may be any nonionic detergent used to separate the surface glycoproteic antigens from the viruses. Triton X-100 is conventionally used for that purpose. This material is an octylphenoxypolyethoxy ethanol derived from the condensation of 9–10 moles ethylene oxide with p-octylphenol. Another useful material is Triton N101 which is a nonylphenoxypolyethoxy ethanol comprising 9–10 ethoxy groups.

The water-insoluble higher alcohol may be any alkanol containing at least 7 carbon atoms and preferably 8 carbon atoms. There is not truly any higher limit except for practical purposes, the $C_{12}+$ alkanols being solid. The selection of the water-insoluble alkanol is directed by the study of its affinity for the detergent used. For example, when a Triton X-100 solution at 1% in a phosphate buffer (containing NaCl 8.85 g/l; $Na_2HPO_4.12 H_2O$ 1.30 g/l and $NaH_2PO_4$ 0.05 g/l) is stirred with an equal volume of various higher alcohols it is found, after washing the aqueous phase with ether at +4° C. and evaporating off the ether, that the residual amounts of Triton X-100 in the buffer, determined by absorption at 276 nm are as follows:

|  | Residual Triton X100 |
|---|---|
| Extraction with primary decyl alcohol | 0.006% w/v |
| Extraction with primary nonyl alcohol | 0.005% w/v |
| Extraction with primary octyl alcohol | 0.002% w/v |

Thus, primary octyl alcohol, or 1-octanol, is found to be preferable in the case of Triton X100.

It is thus apparent that the affinity of the alcohol for the detergent is greater when the hydrophobic chain lengths of the alkanol and the nonionic detergent are similar.

As to the aqueous phase, this may consist of water or a buffer solution, such as a phosphate buffer containing a physiological concentration of sodium chloride.

In practice, the phase separation used according to the present invention may be effected on the aqueous phase obtained after separation of the viral particles, by addition of the higher alcohol and removal of the alcohol phase after separation.

However, when polyethylene glycol is used to separate the viral particles, the glycoproteins pass into the alcohol after addition of the higher alcohol. Therefore, after removal of the original aqueous phase containing the major proportion of the polyethylene glycol, it is convenient to add a second aqueous phase to the phase consisting of the higher alcohol, and to remove the alcohol phase after phase separation.

To remove the trace higher alcohol from the aqueous phase, it is possible, in either case, to add ether to the aqueous phase and subsequently separate the aqueous phase from the ether.

A more detailed description of the process of the present invention as applied to the isolation of hemagglutinin and neuraminidase from influenza virus is given below.

Influenza virus is cultivated in embryonated hen's egg. The virus-containing allantoic liquide is collected. The virus may be concentrated by a number of methods: adsorption, elution with formolized and autoclaved red cells of hens, centrifugation, density gradient centrifugation, precipitation with polyethylene glycol, etc. Various combinations of such methods may also be used.

Inactivation of the virus with β-propiolactone or formol, for example, may be effected at such times.

To the concentrated viral suspension is added a nonionic detergent, such as Triton X100, at a suitable concentration, such as 2% v/v, for example. The mixture is incubated at room temperature for a suitable period of time to result in solubilization of the glycoproteins.

The viral corpuscles are then separated from the glycoproteic antigens by suitable means, such as centrifugation, gradient centrifugation, "precipitation" or rather exclusion of the viral particles by means of polyethylene glycol 6000, the latter method being preferred in view of its greater convenience.

After removal of the viral particles, the glycoproteins-detergent mixture is treated with a suitable volume (generally an equal volume) of water-insoluble higher alcohol, such as 1-octanol.

The mixture is effected at room temperature (at least 20° C.) in a separating funnel, for example. After mixing for a sufficient period of time (5–10 minutes, for example), the emulsion is left at room temperature. Separation of two phases is found to occur: a lower aqueous phase and an upper phase formed of an emulsion resulting from the separation of the insoluble alcohol. The nonionic detergent is then present in the water-insoluble alcohol. Where the glycoproteins are concerned, this depends on the composition of the aqueous phase prior to its admixture with the insoluble alcohol.

This situation of the glycoproteins in the phase system is particularly influenced by the presence of polymers such as polyethylene glycol 6000 (PEG 6000). Practically, essentially two cases may be distinguished:

First case:

PEG 6000 is not used for the separation of viral particles after incubation with the detergent.

Centrifugation is used, for example.

In such case, after removal of the viral corpuscles, the solubilized glycoproteins are present with the non-ionic detergent (e.g., Triton X100) dissolved in a phosphate buffer containing a physiological concentration of sodium chloride.

In such case, the non-ionic detergent is retained in the upper phase emulsion (1-octanol, for example) and the glycoproteins are found in the lower aqueous phase. After a first decantation, the alcohol phase may be washed with a buffer which entrains remaining glycoproteins, the detergent remaining bound to the water-insoluble higher alcohol.

The combined aqueous phases may then be washed with ether to remove any traces of higher alcohol from the aqueous phase.

Second case:

Use of polyethylene glycol.

After incubation of the virus with the nonionic detergent, addition of a suitable amount of polyethylene glycol 6000 (8%, for example) constitutes a convenient means for the separation of the viral corpuscles from the solubilized glycoproteins.

After incubation for 1 hour at +4° C. in the presence of PEG 6000 (at 8% w/v, for example), the mixture is centrifuged for 30 minutes at +4° C. at 2000 G.

If separation of the viral corpuscles occurs at a PEG 6000 concentration below 8%, PEG 6000 is added to attain said 8% concentration prior to admixture with the water-insoluble higher alcohol.

Under such conditions, the glycoproteins leave the aqueous phase and migrate to the higher alcohol phase which, as previously described, has the appearance of an emulsion.

The lower aqueous phase is then removed, and the upper phase is washed with a buffer solution (for example, the phosphate buffer mentioned above).

One may then, for example, effect successively two washings with buffer volumes equal to the volume of water-insoluble higher alcohol, and, optionally, to a third wash with a reduced volume of buffer.

As in the first case, the combined aqueous phases may be washed with ether to remove the traces of water-insoluble higher alcohol.

The resulting glycoprotein solution still contains some PEG 6000. Removal of this polymer may be effected by ultrafiltration under pressure, through a membrane of suitable porosity which permits the passage of PEG 6000 and retains the glycoproteins.

It is also possible to reduce considerably the PEG 6000 content by addition of a suitable salt, such as ammonium sulfate at a rate of 25 g salt added par 100 ml glycoprotein solution at +4° C.

The PEG 6000 then separates as a thin supernatant layer which may be separated by decantation. The ammonium sulfate is then removed by dialysis.

The above methods may be combined: for example: action of a salt with subsequent dialysis through a suitable membrane which insures the dialysis of the salt and the removal of the residual PEG 6000.

Finally, the glycoprotein solution obtained in either case may be sterilized by filtration through a membrane.

Glycoprotein extraction according to this invention results in a most efficient removal of the non-ionic detergent.

For example, when used is made of Triton X-100 at 2% for the solubilization of the glycoproteins, and of 1-octanol (primary octyl alcohol) as water-insoluble higher alcohol, the Triton remains bound to the octanol and, after washing the glycoprotein solution with ether, the resulting aqueous solution is found to contain an amount of Triton X100 below 0.01% w/v.

The resulting glycoprotein solutions may be used for the preparation of vaccines, merely by dilution with an isotonic solution and, typically, with an isotonic phosphate buffer.

The present invention may be applied most particularly to the preparation of influenza vaccine (against A or B type viruses). The influenza vaccines to be administered to humans may contain a dosage of hemagglutinin of 7–20 $\mu$g.

The polyvalent vaccines consist of a mixture of glycoproteins extracted from different strains whose presence is required in the vaccine.

The glycoproteins may be administered by subcutaneous or intramuscular injection as such or in admixture with an adjuvant such as aluminum hydroxide or aluminum phosphate.

The following non limiting Examples illustrate the present invention.

EXAMPLE 1

B/Hong Kong/8/73 influenza virus is cultivated in the allantoic cavity of 11 day embryonated hen's eggs.

After 48 hour incubation at 35° C., the eggs are placed overnight in a cold (+4°C.) room. The virus contained in the allantoic liquid is concentrated by adsorption-elution with formolized-treated and autoclaved red cells of hens. After elution, the virus is suspended in the following buffer:

| | | |
|---|---|---|
| NaCl | 0.85 | g |
| $PO_4HNa_2 12H_2O$ | 1.30 | g |
| $PO_4H_2Na$ | 0.05 | g |
| Distilled water, to make | 1 | liter |

| -continued | |
|---|---|
| pH | 7.5 | after which 8% of polyethylene glycol 6000 s added at +4° C.

After one hour, the resulting material is treated by centrifugation at 2000 G for 30 minutes at +4° C.

The centrifugation pellet in taken up into a volume of buffer equal to 1/10 of that of the starting suspension and containing 2% Triton X100.

After incubation for 2 hours at 25° C., the mixture is left aside overnight at +4° C. 8% Polyethylene glycol 6000 is added thereto the next day.

After a residence time of 1 hour at +4° C., the mixture is treated by centrifugation at 3000 G for 30 minutes at +4° C.

The supernatant is collected and, after warming to 22° C., is mixed with an equal volume of 1-octanol in a separating funnel; it is then stirred for 10 minutes, after which the phases are left to separate at 22° C. for one hour. The cloudy aqueous phase is removed and replaced in the funnel by an equal volume of phosphate buffer having the above-described composition and which contains no polyethylene glycol. The mixture is stirred for 10 minutes and is then allowed to stand one hour at 22° C.

The aqueous phase is collected, set aside, and the operation is repeated. Both the turbid aqueous phases are combined, cooled to +4° C. and admixed with an equal volume of cold ether. The resulting material is mixed by cautious tumbling and stirring in a separation funnel and the phases are allowed to separate overnight at +4° C.

The next day, the clear aqueous phase is separated and the ether is removed therefrom by evaporation in vacuo.

The polyethylene glycol is removed by ultrafiltration.

The determination of the residual amount of Triton X100 in the glycoprotein solution is effected by precipitation of the glycoproteins with 5 volumes of methanol. After one night at room temperature, the material is submitted to a centrifugation for 30 minutes at 2000 G.

After removal of the methanol from the supernatant by evaporation, distilled water is added to bring the residue to the original volume of the sample and the amount of Triton X100 is determined spectrophotometrically at 276 nm with respect to a standard consisting of a buffer which has been submitted to the same methanol treatment, in order to remove the influence of potential impurities in the methanol. The resulting product of this invention contains only 0.007% w/v residual Triton.

The glycoproteins appear pure by polyacrylamide gel electrophoresis.

Examination with an electronic microscope shows glycoprotein aggregates, exclusive of any other component.

The hemagglutinating activity, the actual amount of antigenic hemagglutinin by radial immunodiffusion, and the neuraminidase activity were determined from the resulting solution.

This enzymatic activity of the neuraminidase was investigated according to the method of M. AYMARD-HENRY and co-workers, 1973, Bull. Org. Mond. Sante, Vol. 48, pp. 199-202, by the dilution of the preparation giving an optical density of 0.25 at 549 nm.

Comparative activities for equivalent volumes of initial viral suspension and glycoproteic extract:

| | Viral suspension | Glycoprotein solution |
|---|---|---|
| Hemagglutination | 4020 IU/ml | 3592 IU/ml |
| Radial immunodiffusion | 25 μg HA/ml | 20 μg HA/ml |
| Neuraminidase activity | 1/200 | 1/100 |

EXAMPLE 2

The procedure of Example 1 used, with A/Texas/1/77 virus strain. The following results are obtained: Residual Triton: 0.007% w/v.

| | Viral suspension | Glycoprotein solution |
|---|---|---|
| Hemagglutination | 4240 IU/ml | 4788 IU/ml |
| Radial immunodiffusion | 60 μg | 27 μg |
| Neuraminidase activity | undetermined | 1/30 |

EXAMPLE 3

The procedure of example 1 is repeated, using as virus X71 recombinant strain, antigenically identical with A/Brazil/11/78. The following results are obtained:

| Residual Triton: 0.005% w/v. | | |
|---|---|---|
| | Viral suspension | Glycoprotein solution |
| Hemagglutinin | 10500 IU/ml | 2500 IU/ml |

EXAMPLE 4

A/Victoria/75 influenza virus is cultivated in the allantoic cavity, collected and concentrated by adsorption-elution with formolized-treated and autoclaved red cells of hens, as in Example 1. It is resuspended in the same buffer and precipitated with 8% PEG 6000; the precipitate is collected by centrifugation, replaced in a buffer volume equal to 1/10 of the original volume containing 2% Triton X100. After 2 hours incubation at 25° C., the mixture is left aside overnight at +4° C. The next day, the particles are removed by filtration, or by centrifugation of the supernatant and treated with an equal volume of 1-octanol, as in Example 1. After decantation, the aqueous phase is collected. It is replaced in the funnel by an equal volume of buffer having the same composition, the material is stirred 10 minutes and allowed to stand for 1 hour at 22° C. Both aqueous phases are combined, cooled to +4° C. and treated with an equal volume of cold ether, as in Example 1. The clear aqueous phase is finally collected and the ether is removed by evaporation in vacuo. The following results are obtained:

| | Prior to treatment | After treatment |
|---|---|---|
| Hemagglutinin | 50 μg/ml | 17 μg/ml |
| Neuraminidase | 1/60 | 1/48 |
| Residual Triton: 0.003%. | | |

EXAMPLE 5

A vaccine having the following composition is prepared:

Mixture containing 10 μg of hemagglutinin, obtained in Example 1.

Isotonic phosphate buffer: to make 1 ml.

We claim:

1. Process for the isolation of the glycoproteic antigens of a virus by treatment of said virus with an aqeous solution of a nonionic detergent, separation of the viral particles and removal of the detergent, comprising, in order to remove the detergent, effecting a phase separation between an aqueous phase and a phase consisting of a water-insoluble alkanol having at least 7 and less than 12 carbon atoms, and recovering the glycoproteic antigens in aqueous phase.

2. Process as claimed in claim 1, wherein the water-insoluble alkanol is an alkanol having at least 8 carbon atoms.

3. Process as claimed in claim 1, wherein the nonionic detergent is an octylphenoxypolyethoxyethanol derived from the condensation of 9-10 moles ethylene oxide with p-octylphenol.

4. Process as claimed in claim 3, wherein said alkanol having at least 7 and less than 12 carbon atoms is 1-octanol.

5. Process as claimed in claim 1, wherein the aqueous phase used for the phase separation is that obtained after separation of the viral particles in the absence of polyethylene glycol.

6. Process as claimed in claim 1, wherein, in the case the viral particle separation is effected with polyethylene glycol, the alkanol having at least 7 and less than 12 carbon atoms is added to the resultant phase containing the polyethylene glycol, the glycoproteic antigens and the nonionic detergent; the aqueous phase is removed after the phase separation step, a second aqueous phase is added to the phase consisting of the alkanol having at least 7 and less than 12 carbon atoms and, after phase separation, the glycoproteic antigens are recovered in the second aqueous phase.

7. Process as claimed in claim 1, wherein the aqueous phases separated from the water-insoluble alkanol having at least 7 and less than 12 carbon atoms are washed with ether.

8. Process as claimed in claim 1, wherein the aqueous phase consists of a phosphate buffer.

9. Process for the preparation of a vaccine, wherein the glycoproteic antigens obtained by a process as claimed in claim 1 are diluted with an isotonic solution.

10. Process as claimed in claim 8, wherein the virus treated is a type A or type B influenza virus.

11. Process as claimed in claim 10, wherein the glycoproteic antigens are diluted in a manner such that the mixture contains from 7 microgrammes to 20 microgrammes hemagglutinin from each virus strain.

* * * * *